United States Patent
Marzilger et al.

(10) Patent No.: US 9,517,156 B2
(45) Date of Patent: Dec. 13, 2016

(54) DEVICE FOR FIXING A TEST PERSON ON A STANDING SURFACE

(71) Applicant: Airbus DS GmbH, Taufkirchen (DE)

(72) Inventors: Robert Marzilger, Brieselang (DE); Rolf Kolb, Friedrichshafen (DE); Ulrich Kübler, Markdorf (DE); Peter Kern, Salem (DE); Steffen Jung, Brühl (DE); Albert Gollhofer, Stegen (DE)

(73) Assignee: Airbus DS GmbH, Taufkirchen (DE)

( * ) Notice: Subject to any disclaimer, the term of this patent is extended or adjusted under 35 U.S.C. 154(b) by 0 days.

(21) Appl. No.: 14/878,004

(22) Filed: Oct. 8, 2015

(65) Prior Publication Data

US 2016/0030225 A1 Feb. 4, 2016

Related U.S. Application Data

(62) Division of application No. 13/579,354, filed as application No. PCT/DE2011/000107 on Feb. 5, 2011, now Pat. No. 9,205,935.

(30) Foreign Application Priority Data

Feb. 20, 2010 (DE) .................. 10 2010 008 651
May 12, 2010 (DE) .................. 10 2010 020 395

(51) Int. Cl.
*A61F 5/37* (2006.01)
*A63B 21/00* (2006.01)
(Continued)

(52) U.S. Cl.
CPC .............. *A61F 5/3784* (2013.01); *A61F 5/37* (2013.01); *A63B 21/15* (2013.01);
(Continued)

(58) Field of Classification Search
CPC ........... B64G 1/60; A61F 5/37; A61F 5/3784; A63B 21/1419; A63B 26/003; A63B 7/00; A63B 21/0442; A63B 2208/0204; B64D 25/06
See application file for complete search history.

(56) References Cited

U.S. PATENT DOCUMENTS 1,623,670 A 4/1927 Frankenfeld
3,330,052 A 7/1967 Johnson et al.
(Continued)

FOREIGN PATENT DOCUMENTS

CN 1948086 A 4/2007
CN 1973806 A 6/2007
(Continued)

OTHER PUBLICATIONS

International Search Report and Written Opinion of the International Searching Authority dated Jun. 24, 2011 for the corresponding International patent application No. PCT/DE2011/000107 (and English translation).
(Continued)

*Primary Examiner* — Sundhara Ganesan
(74) *Attorney, Agent, or Firm* — Posz Law Group, PLC

(57) ABSTRACT

The invention relates to a device for fixing a test person on a standing surface, wherein at least one rope is tensioned between a hip belt placed on the test person and a retaining plate arranged below the standing surface.

9 Claims, 4 Drawing Sheets

Figure 1:
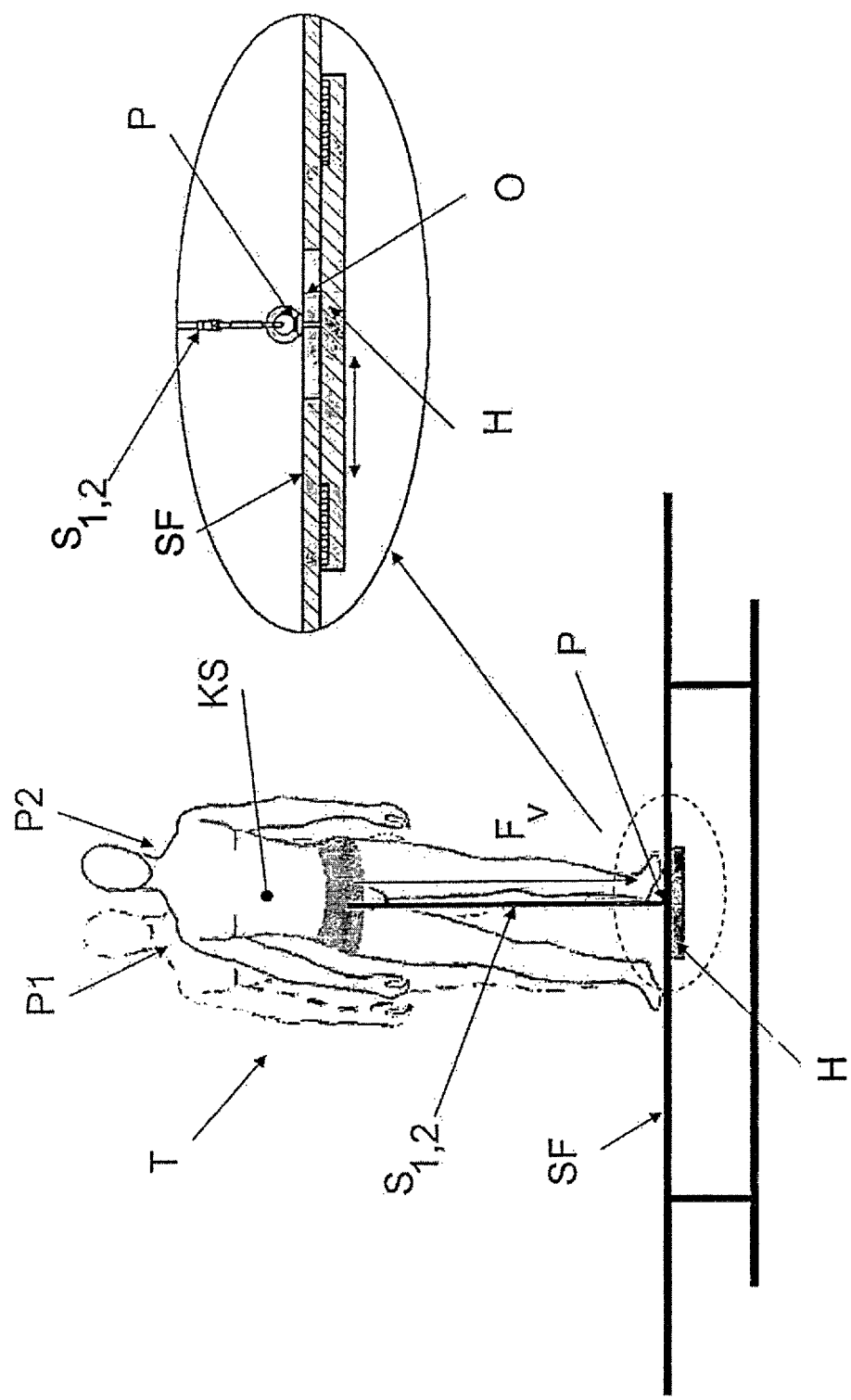

(51) Int. Cl.
*B64G 1/60* (2006.01)
*B64D 25/06* (2006.01)
*A61H 3/00* (2006.01)
*A63B 26/00* (2006.01)

(52) U.S. Cl.
CPC ............ *A63B 21/4009* (2015.10); *B64G 1/60* (2013.01); *A61H 3/008* (2013.01); *A63B 26/003* (2013.01); *B64D 25/06* (2013.01)

(56) References Cited

U.S. PATENT DOCUMENTS

| | | | |
|---|---|---|---|
| 3,583,322 A | 6/1971 | Vykukal | |
| 4,586,658 A | 5/1986 | Eisenegger | |
| 4,709,782 A | 12/1987 | Lipinski | |
| 4,915,325 A | 4/1990 | Ryder | |
| 4,968,028 A | 11/1990 | Wehrell | |
| 4,976,623 A * | 12/1990 | Owsley | A63B 69/0064 |
| | | | 434/247 |
| 5,042,173 A | 8/1991 | Blizzard et al. | |
| 5,421,783 A * | 6/1995 | Kockelman | A63B 5/16 |
| | | | 472/131 |
| 5,512,029 A | 4/1996 | Barnard et al. | |
| 5,586,692 A | 12/1996 | Livengood | |
| 5,593,368 A | 1/1997 | Checketts | |
| 5,795,277 A | 8/1998 | Bruntmyer | |
| 5,924,933 A | 7/1999 | Pacheco | |
| 6,030,321 A | 2/2000 | Fuentes | |
| 6,402,667 B1 | 6/2002 | Dahn | |
| 7,104,932 B1 | 9/2006 | Brentlinger | |
| 7,175,569 B1 | 2/2007 | Lan et al. | |
| 7,314,437 B2 | 1/2008 | Frappier | |
| 7,442,151 B1 | 10/2008 | Berdegue | |
| 7,625,320 B2 | 12/2009 | Wehrell | |
| 7,651,450 B2 * | 1/2010 | Wehrell | A61H 1/0229 |
| | | | 482/124 |
| 7,758,095 B2 * | 7/2010 | Elhanany | B60N 2/24 |
| | | | 296/63 |
| 8,414,026 B1 * | 4/2013 | Lou | B64D 25/06 |
| | | | 280/804 |
| 2003/0153438 A1 | 8/2003 | Gordon et al. | |
| 2006/0189453 A1 | 8/2006 | LeBlond | |
| 2006/0199706 A1 | 9/2006 | Wehrell | |
| 2008/0070757 A1 | 3/2008 | Albert | |
| 2010/0062881 A1 * | 3/2010 | Horkan | A63B 69/00 |
| | | | 473/439 |
| 2011/0021329 A1 | 1/2011 | Dunne | |
| 2011/0045954 A1 * | 2/2011 | Gutierrez | A63B 21/00 |
| | | | 482/51 |
| 2011/0057500 A1 | 3/2011 | Walker et al. | |

FOREIGN PATENT DOCUMENTS

| | | |
|---|---|---|
| CN | 101070096 A | 11/2007 |
| DE | 10 2005 015 715 A1 | 6/2007 |
| DE | 10 2006 022 252 A1 | 12/2007 |

OTHER PUBLICATIONS

Office Action dated Oct. 14, 2010 issued in corresponding DE patent application No. 10 2010 020 395.5 (and English translation).
Office Action mailed Jan. 7, 2014 issued in corresponding JP patent application No. 2012-553175 (and English translation).
Office Action dated Apr. 22, 2014 issued in corresponding CN patent application No. 201180010232.X (and English translation).
Office Action dated Dec. 23, 2014 issued in corresponding CN patent application No. 201180010232.X (and English translation).

* cited by examiner

DEVICE FOR FIXING A TEST PERSON ON A STANDING SURFACE

CROSS REFERENCE TO RELATED APPLICATIONS

This application is a divisional of U.S. patent application Ser. No. 13/579,354 filed on Feb. 26, 2013, which is a U.S. national stage application of PCT/DE2011/000107 filed on Feb. 5, 2011, and claims priority to, and incorporates by reference, German patent applications No. 10 2010 008 651.7 filed on Feb. 20, 2010 and No. 10 2010 020 395.5 filed on May 12, 2010.

The invention relates to a device for fixing a test person on a standing surface.

In particular, the invention relates to a device that allows persons to be fixed under weightlessness, such that they can apply forces to their standing surface (supporting surface).

Customary devices are based on foot bindings and rope systems. The foot bindings generally serve for movement and fixing in stationary work, but a use for sports activities is not ruled out. The rope systems are mostly anchored in, the floor and fix the person, with the aid of a harness on the upper body, to the structure of the spacecraft. The foot bindings do not permit permanent fixing. Moreover, they are not suitable for fixing a test person with variable force on the supporting surface. Although the rope systems permit variable fixing of the person, their arrangement means that they also offer great lateral constraining forces.

Standard exercises, e.g. standing on one leg or on both legs with the eyes closed, are based on the test person being intended to remain standing as still as possible for a defined time interval, with any movement being recorded and evaluated. Such exercises are possible only to a limited extent with the customary devices.

The object of the invention is to make available a device for fixing a test person on a standing surface, in which the lateral constraining forces are reduced, while variable vertical forces can still act on the test person.

This object is achieved with the device having the features of current claim 1. Advantageous embodiments are the subject matter of dependent claims.

According to the invention, at least one rope is tensioned between a waist belt, which is placed on the test person, and a retaining plate, which is arranged below the standing surface.

The fixing is such that it can exert on the test person a variable vertical (gravity-simulating) force and minimizes the horizontal forces that arise. The nature of the fixing allows the person maximum freedom of movement, without having to exert restoring or supporting forces for the movement, which is an important requirement especially for coordinated balance training.

At least two ropes are expediently tensioned between the waist belt and the retaining plate. Moreover, the standing surface advantageously has an opening, through which the ropes are guided. This opening is suitably located in the area of the center of gravity of the test person, as projected vertically onto the standing surface. The ropes are expediently guided in such a way that the ropes do not touch the test person. Depending on the height of the test person, i.e. on the height of the waist belt above the standing surface, it may be necessary to fasten the ropes to the waist belt by means of a horizontal spacing.

Figure 2:
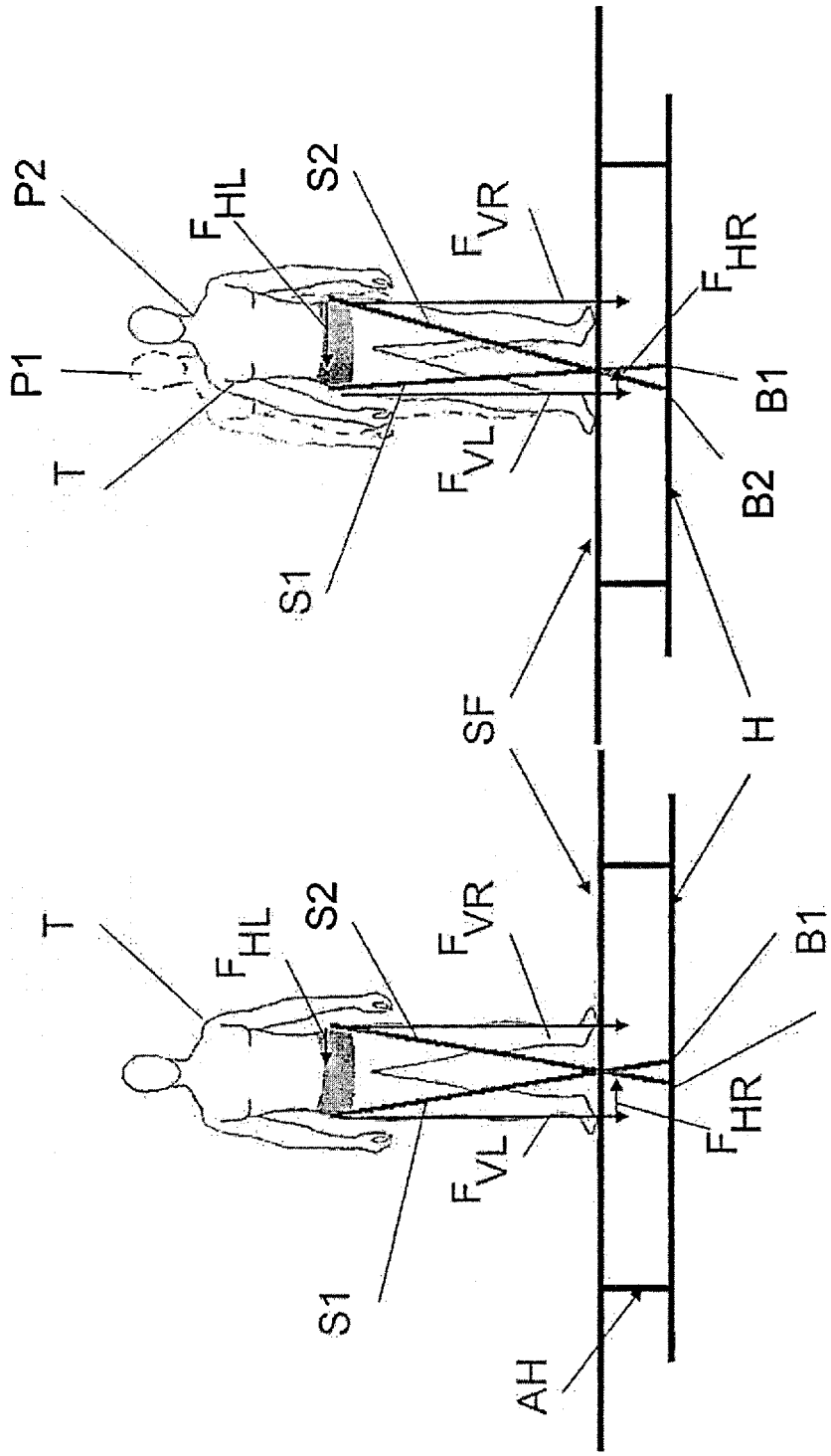
Figure 3:
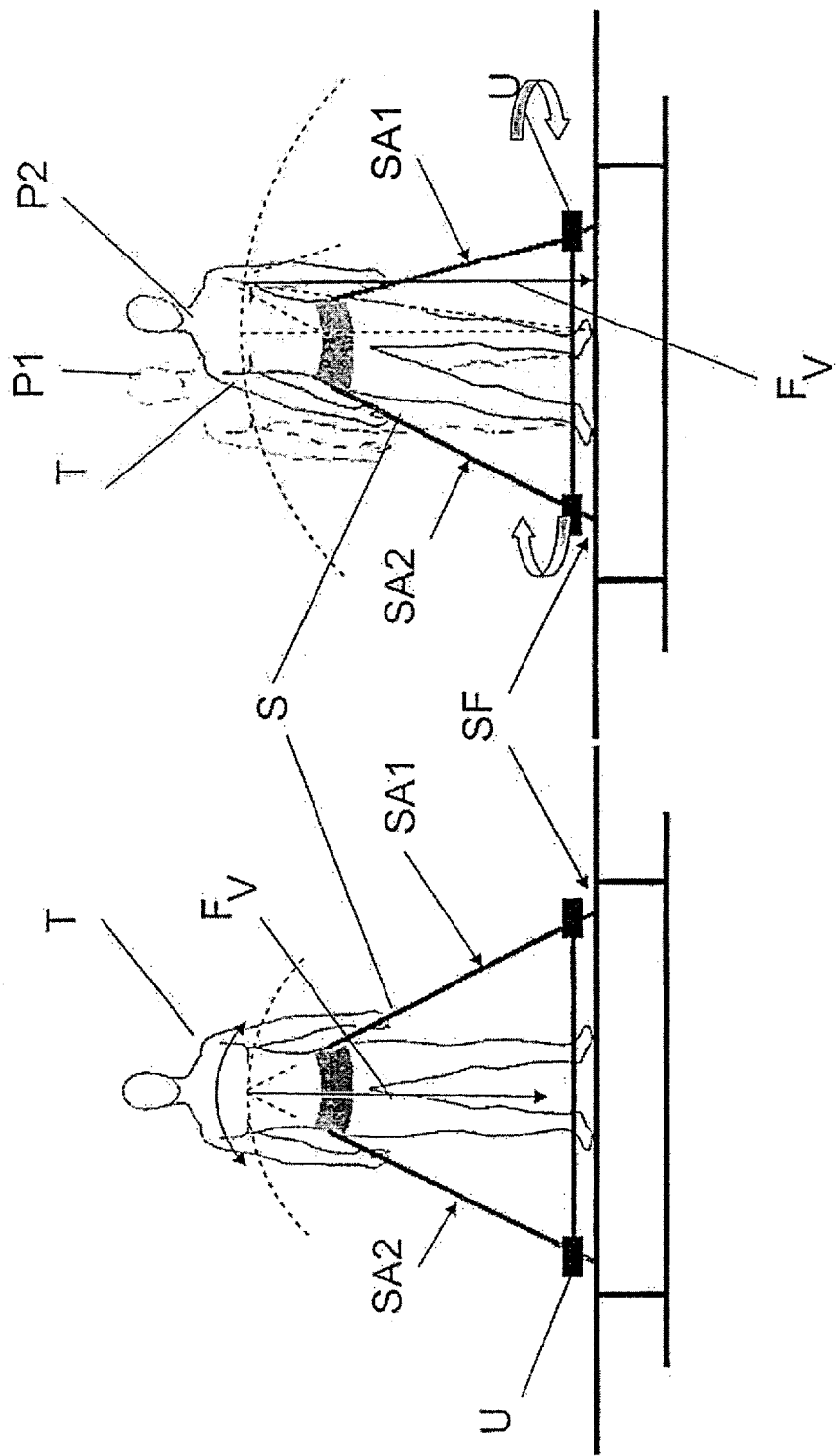
Figure 4:
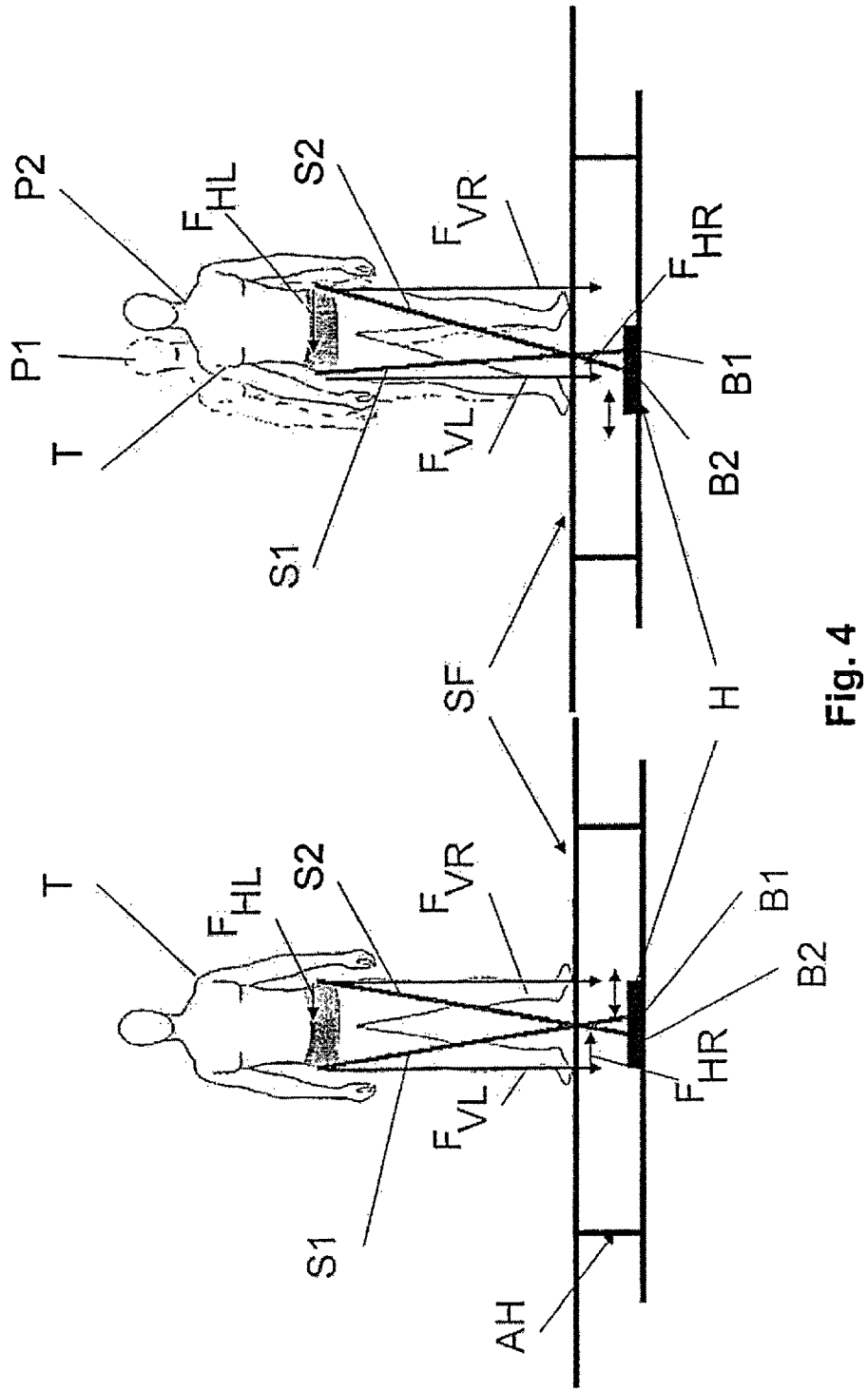

The invention and advantageous embodiments thereof are explained in more detail with reference to figures, in which:

FIG. 1 shows a first embodiment of the invention,
FIG. 2 shows a second embodiment of the invention,
FIG. 3 shows a third embodiment of the invention,
FIG. 4 shows a fourth embodiment of the invention.

In the first embodiment, shown in FIG. 1, elastic ropes S are expediently brought together at a fastening point P on the retaining plate H. Two ropes are provided by way of example in FIG. 1, one rope $S_1$ being fastened at the front in the area of the stomach of the to person T, and the other rope $S_2$ being fastened at the rear in the area of the back.

The fastening point P is in this case expediently chosen such that it is situated in the plane enclosed by the normal to the standing surface SF and the projection of the body's center of gravity KS onto the standing surface SF. A dedicated fastening point P in said plane can expediently be chosen for each rope.

The standing surface SF expediently has an opening O (enlarged view), which is formed in the area of the center of gravity KS of the test person, as projected vertically onto the standing surface SF. The retaining plate H expediently has an extent greater than the opening O. The retaining plate H is mounted below the standing surface SF in such a way that it can move freely in the horizontal plane (arrow direction). The ropes $S_1$ and $S_2$ are guided through the opening O and connect the waist belt of the test person T to the retaining plate H. In a horizontal excursion of the waist belt (from position P1 to position P2) of the test person T, the fixing at the fastening point P follows the movement, of the body's center of gravity KS, as a result of which the elastic ropes $S_1$ and $S_2$ in turn do not experience any changes in length and force during movements in the horizontal plane. In this system, therefore, the only acting force is a vertical force $F_v$, which results from the stretching of the restraint ropes $S_1$ and $S_2$.

In a second embodiment of the invention, shown in FIG. 2, the test person T is fixed on the standing surface SF with, for example, the aid of two intersecting elastic ropes $S_1$ and $S_2$. To make the figure clearer, the ropes $S_1$ and $S_2$ are each applied to the side of the waist belt of the test person T. However, it may also be expedient to use four ropes, in which case a further rope is fastened in the area of the stomach and another in the area of the back of the test person T, optionally also offset by 45°, i.e. laterally outward in front of or behind the hip (not shown).

The retaining plate H is expediently arranged at a distance d below the underside of the standing surface SF. The retaining plate H is not movable in this embodiment, e.g. the retaining plate is connected fixedly to the underside of the standing surface SF by means of a spacer AH. The explanations set forth concerning the opening O in the first embodiment apply also in this embodiment.

The fastening points $B_1$ and $B_2$ of the elastic ropes $S_1$ and $S_2$ on the retaining plate H are chosen such that the ropes $S_1$ and $S_2$ intersect at the intersection SP with the standing surface SF. The advantage of this arrangement lies in the very small space required and in the very low horizontal forces. Firstly, as a result of the relatively large angle that the ropes $S_1$ and $S_2$ enclose with the standing surface SF, the cosine component of the tensile force is much lower than with bracing to the sides, and, secondly, the X-shaped arrangement of the ropes $S_1$ and $S_2$ causes alternating horizontal forces $F_{HL}$. Thus, the horizontal restoring forces $F_{HL}$ initially increase during a movement from position 1 to position 2, and they reach their maximum when the rope $S_1$ is perpendicular to the standing surface SF, after which the restoring force decreases again.

The third embodiment of the invention is shown in FIG. 3. At least three deflection rollers U (for drawing reasons only 2 rollers are indicated) are arranged on the retaining plate H in such a way that the center of gravity of the area (not shown) formed by the deflection rollers U coincides with the center of gravity KS of the test person T, as projected onto the retaining plate H, and one circumferential rope S is guided from the waist belt, placed on the test person T, across the deflection rollers U and back to the waist belt.

The circumferential steel rope S can be tensioned with the aid of a hand winch. Spring balances can be used to determine the tensioning force. As a result of the constant rope length, and assuming rollers more or less free of friction, the rope always follows the waist movement in the horizontal plane. It is clear from FIG. 3 that a waist movement to the right (position 1 to position 2) leads to a slackening of the rope S on the right-hand side. This shortening of the rope section SA1 (section between deflection roller and waist belt) on the right-hand side follows a lengthening of the rope section SA2 on the left-hand side, since the rope S has a constant length. Because of the slackening of the rope on one side and the simultaneous lengthening of the rope on the other side, the horizontal forces in the system are very substantially reduced. If the waist movement is assumed as an orbit, then there are also minimal vertical movements of the waist, but this has almost no effect on the force equilibrium in the system. If one assumes a body sway of ±10° on the indicated orbit, then, in the solution shown, there is a maximum length difference in the rope of 5 mm. The resulting reduction of the vertical force component $F_v$ is very slight.

The fourth embodiment of the invention is shown in FIG. 4. This embodiment is a combination of the first and second embodiments. The movable retaining plate H from the first embodiment (FIG. 1) is arranged below the standing surface by a distance AH. This generates tensioning similar to the cruciate ligaments in the knee joint. The rolling/sliding mechanism resulting from the described arrangement has the effect that the restraint in the horizontal plane follows the movement of the body's center of gravity KS, and possible tilting movements of the body are at the same time compensated by the intersecting ropes S1, S2.

The device according to the invention can be used advantageously in weightlessness, in water or under normal conditions.

With the device according to the invention, vertical forces can be generated on account of the geometry and mechanics, but possible horizontal forces are reduced. The generated vertical forces are necessary in order to fix the person on the platform under weightlessness, or in order to apply an additional load, similar to a weighted vest.

The reduction of the horizontal forces has the sense that a stabilization of the movement by the restraint is prevented.

The aim of such a restraint is not to make training easier for the person training, e.g. by the additional lateral guide, but to maintain the degree of difficulty of the training (weightlessness) or increase the degree of difficulty of the training (on Earth.). This can be achieved by the additional vertical force, which is applied with the aid of the restraint/fixing.

In the advantageous use of the device according to the invention in water, the buoyancy force on a body immersed in water is used to make the body virtually weightless. Through the use of the device according to the invention in water, e.g. in a tank provided for this purpose, a person training can be provided with a training regimen which permits training in which the exercises can be performed under adjustable loading for the person training. The loading for the person training can be adjusted, on the one hand, by how deep the person training is immersed in the water and, on the other hand, by setting the additional vertical force by the fixing, according to the invention, of the person training on the standing surface. The force acting on the person training results from the height of the water level in the tank in which the person training is situated, and from the vertical force which counteracts the buoyancy force and with which the person training is fixed on the standing surface.

Especially in the rehabilitation of injuries, e.g. sports injuries, it is therefore possible, immediately after the medical treatment, to return to the training of important movements, initially under reduced loading. The loading reduced by the water also allows the development to be used in the geriatric sector or in therapy. The loading can be increased again as training progresses.

The implementation of the advantageous use is known in principle from other training variants, e.g. from treadmill training under water, but not for the performance of sensorimotor training. The advantageous use of the device according to the invention in water therefore represents a development that affords further advantages for the person training.

Besides rehabilitation, therapy, geriatrics and sport, the advantageous use of the device according to the invention in water also affords a very effective development of the abovementioned use for the training of astronauts. By completion of sensorimotor exercises before a space flight, which exercises can then be repeated under identical conditions during the space flight, it is postulated that the adaptation to weightlessness, with the known problems such as coordination difficulties and space sickness, can be overcome more quickly than by the known methods.

Therefore, even before the start of a mission, the different gravitational conditions of a target planet can be simulated on earth and trained for. Scientific experiments already carried out lead to the assumption that sensorimotor capabilities, once acquired, can be maintained by relatively short and regular exercises.

The invention claimed is:

1. A device for fixing a test person on a standing surface, wherein between a waist belt placed on the test person and a retaining plate arranged below the standing surface at least one rope is tensioned,
   wherein at least three deflection rollers are arranged on the retaining plate in such a way that the center of gravity of the area formed by the deflection rollers coincides with the center of gravity of the test person, as projected onto the retaining plate, and one circumferential rope is guided from the waist belt, placed on the test person, across the deflection rollers and back to the waist belt,
   wherein the rope is a flexible steel rope.

2. Use of a device as claimed in claim 1, in weightlessness or in water.

3. The device as claimed in claim 1, wherein the deflection rollers are arranged uniformly distributed around the center of gravity of the area formed by the deflection rollers.

4. The device as claimed in claim 1, wherein the deflection rollers are arranged uniformly distributed around the center of gravity of the test person, as projected onto the retaining plate.

5. The device as claimed in claim 1, wherein each of the deflection rollers has a pivot which is arranged in a common plane.

6. The device as claimed in claim 1, wherein the circumferential rope is guided from the waist belt, placed on the test person, across the deflection rollers and directly back to the waist belt.

7. The device as claimed in claim 1, wherein the waist belt comprises at least one inner ring, placed directly on the test person, and at least one outer ring which guides the rope, wherein the inner ring is pivot-mounted at the outer ring.

8. The device as claimed in claim 1, wherein the rope has a substantially constant length.

9. The device as claimed in claim 8, wherein a maximum length difference in the rope is 5 mm.

* * * * *